United States Patent
Sevenster et al.

(10) Patent No.: US 11,636,933 B2
(45) Date of Patent: Apr. 25, 2023

(54) SUMMARIZATION OF CLINICAL DOCUMENTS WITH END POINTS THEREOF

(71) Applicants: KONINKLIJKE PHILIPS N.V., Eindhoven (NL); THE UNIVERSITY OF CHICAGO, Chicago, IL (US)

(72) Inventors: Merlijn Sevenster, Haarlem (NL); Sandeep Madhukar Dalal, Winchester, MA (US); Amir Mohammad Tahmasebi Maraghoosh, Arlington, MA (US); Paul Joseph Chang, Chicago, IL (US)

(73) Assignee: Koninklijke Philips N.V., Eindhoven (NL)

( * ) Notice: Subject to any disclaimer, the term of this patent is extended or adjusted under 35 U.S.C. 154(b) by 317 days.

(21) Appl. No.: 16/500,825

(22) PCT Filed: Apr. 19, 2018

(86) PCT No.: PCT/EP2018/060090
§ 371 (c)(1),
(2) Date: Oct. 4, 2019

(87) PCT Pub. No.: WO2018/193051
PCT Pub. Date: Oct. 25, 2018

(65) Prior Publication Data
US 2020/0118660 A1  Apr. 16, 2020

Related U.S. Application Data

(60) Provisional application No. 62/488,289, filed on Apr. 21, 2017.

(51) Int. Cl.
*G16H 15/00* (2018.01)
*G06N 20/00* (2019.01)
(Continued)

(52) U.S. Cl.
CPC ............ *G16H 15/00* (2018.01); *G06F 40/205* (2020.01); *G06K 9/6262* (2013.01); *G06N 20/00* (2019.01)

(58) Field of Classification Search
CPC ........ G16H 70/60; G16H 10/60; G16H 15/30; G16H 15/00; G06F 19/00; G06F 17/30;
(Continued)

(56) References Cited

U.S. PATENT DOCUMENTS

2010/0023346 A1* 1/2010 Paty .................... G06Q 30/0203
705/2
2010/0145720 A1* 6/2010 Reiner .................... G16Z 99/00
705/2
(Continued)

FOREIGN PATENT DOCUMENTS

WO  2014042942 A1  3/2014

*Primary Examiner* — Fonya M Long
*Assistant Examiner* — Alaaeldin M Elshaer (57) ABSTRACT

A system (100) includes an end point prediction engine (150) that predicts an end point (302) using a machine learning model (132) and one or more clinical report objects (152) for a patient, wherein the machine learning model inputs the one or more clinical report objects and outputs the predicted end point according to phrases or n-grams in the one or more clinical report objects. An end point visualization interface (160) visualizes the predicted end point (302) using a scorecard (162) or a timeline (164). An end point modeling engine (130) generates the machine learning model from training data that includes validated end points (122) and clinical report objects (116).

11 Claims, 4 Drawing Sheets

(51) Int. Cl.
*G06F 40/205* (2020.01)
*G06K 9/62* (2022.01)

(58) Field of Classification Search
CPC .. G06F 40/205; G06F 19/322; G06F 19/3487; G06N 5/00; G06N 20/00; G06N 3/08; G06N 99/005; G06Q 10/10; G06K 9/6262
USPC .......................................................... 705/2, 3
See application file for complete search history.

(56) References Cited

U.S. PATENT DOCUMENTS

| | | | |
|---|---|---|---|
| 2012/0203575 A1* | 8/2012 | Tulipano | G16H 15/00 705/3 |
| 2012/0290319 A1 | 11/2012 | Saria et al. | |
| 2014/0324469 A1* | 10/2014 | Reiner | G16H 10/60 705/3 |
| 2014/0365232 A1* | 12/2014 | Sadeghi | G16H 50/20 705/2 |
| 2014/0379378 A1* | 12/2014 | Cohen-Solal | G16H 15/00 705/3 |
| 2016/0147946 A1 | 5/2016 | Von Reden | |
| 2016/0328526 A1* | 11/2016 | Park | G16Z 99/00 |
| 2018/0052956 A1 | 2/2018 | Sevenster et al. | |
| 2018/0060738 A1* | 3/2018 | Achin | G06N 20/00 |

\* cited by examiner

| | Repeat imaging study | Oncological malignancy | Life time expectancy | Qualify screening program | Reports |
|---|---|---|---|---|---|
| Patient | < 30 days | < 30 days | < 5 yrs. | < 30 days | |
| 1 | X | 15% | X | N | A |
| 2 | - | < 1% | - | Y | B, C |
| 3 | - | - | - | N | |
| 4 | X | 85% | - | Y | D, E, F, G |
| 5 | - | 10% | - | N | H |
| 6 | - | 20% | - | N | I |

SUMMARIZATION OF CLINICAL DOCUMENTS WITH END POINTS THEREOF

CROSS-REFERENCE TO PRIOR APPLICATIONS

This application is the U.S. National Phase application under 35 U.S.C. § 371 of International Application No. PCT/EP2018/060090, filed on Apr. 19, 2018, which claims the benefit of U.S. Patent Application No. 62/488,289, filed on Apr. 21, 2017. These applications are hereby incorporated by reference herein.

FIELD OF THE INVENTION

The following generally relates to medical informatics, and more specifically to the summarization of clinical reports.

BACKGROUND OF THE INVENTION

Each time a patient is examined or tested, a healthcare practitioner typically generates a medical document or clinical report, which describes the examination or test and states the result. The clinical report stores information in structured, codified, or narrative text and/or combinations thereof. An example of a structured report is an electronic lab report in which a computer is used to enter information items into fields of a predetermined template. With this example, each information item is entered into a form according to a predetermined ontology or lexicon, such as Systematized Nomenclature of Medicine (SNOMED), RadLex®, International Classification of Diseases (ICD), RxNorm, and the like.

For example, with the ICD ontology a ICD diagnosis code of 134.0 represents "Nonrheumatic mitral (valve) insufficiency." When the healthcare practitioner enters or selects the code 134.0 in a field of the form for a structured report, the code is stored within the form. A system may populate the field in a presentation of the form with the text "Non-rheumatic mitral (valve) insufficiency," and in generating a final report replace the code with the text. An example of a codified clinical report includes an echocardiogram clinical report, in which information items are structured by and entered using internal unique identifiers, and each internal unique identifier is mapped to and represented with a corresponding narrative text element. Examples of narrative clinical reports include radiology reports, pathology reports, surgery reports, laboratory report and progress reports, in which information items are embedded in prose language.

Healthcare practitioners, such as a radiologist, review prior clinical reports for a patient when conducting an examination, such as an imaging study. Reviews can be voluminous and time consuming in the amount of information in each report and in the number of reports reviewed. One conventional approach to improve the review process and enable direct and fast access to information within the clinical report is to generate structured clinical documents from a dictated narrative using natural language processing techniques (NLP) either at the point of patient care or after the fact. However, this approach calls for considerable overhead by a report creator, such as a subspecialized physician, or includes large error margins.

SUMMARY OF THE INVENTION

Aspects described herein address the above-referenced problems and others.

The following describes embodiments of a system and method for summarization of clinical reports. Clinical reports are converted into objects, such as Extensible Markup Language (XML), Javascript Object Notation (JSON), and the like. Clinical end points are validated in a collection of the clinical report objects. A clinical endpoint is a meaning or a main message of that report, such as a diagnosis, a recommendation for a follow-up study, or a cost of a treatment. The clinical end point is a quantifiable parameter that can assume a finite number of discrete values. In some embodiments, the collection of clinical report objects is supplemented with other patient related data. The collection of clinical report objects with the validated end points are modelled to create a machine learning model. In response to a request to summarize one or more clinical documents for a patient, the machine learning model assesses a value of each of the clinical documents for the patient relative to the end point occurring within a predetermined timeframe. In some embodiments, the assessment is displayed as a scorecard and/or a timeline.

In one aspect, a system includes an end point prediction engine and an end point visualization interface. The end point prediction engine predicts an end point using a machine learning model and one or more clinical report objects for a patient, wherein the machine learning model inputs the one or more clinical report objects and outputs the predicted end point according to phrases or n-grams in the one or more clinical report objects. The end point visualization interface visualizes the predicted end point.

In another aspect, a system includes an end point modeling engine that generates a machine learning model from training data that includes validated end points and clinical report objects.

In another aspect, a computer program product predicts an end point using a machine learning model for one or more clinical report objects for a patient and visualizes the predicted end point.

In another aspect, a computer program product generates a machine learning model from training data that includes validated end points and clinical report objects.

In another aspect, a non-transitory computer-readable storage medium carrying instructions controls one or more processors to generate a machine learning model from training data that includes validated end points and clinical report objects.

These and other aspects of the invention will be apparent from and elucidated with reference to the embodiment(s) described hereinafter.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

DETAILED DESCRIPTION OF EMBODIMENTS

Figure 1:
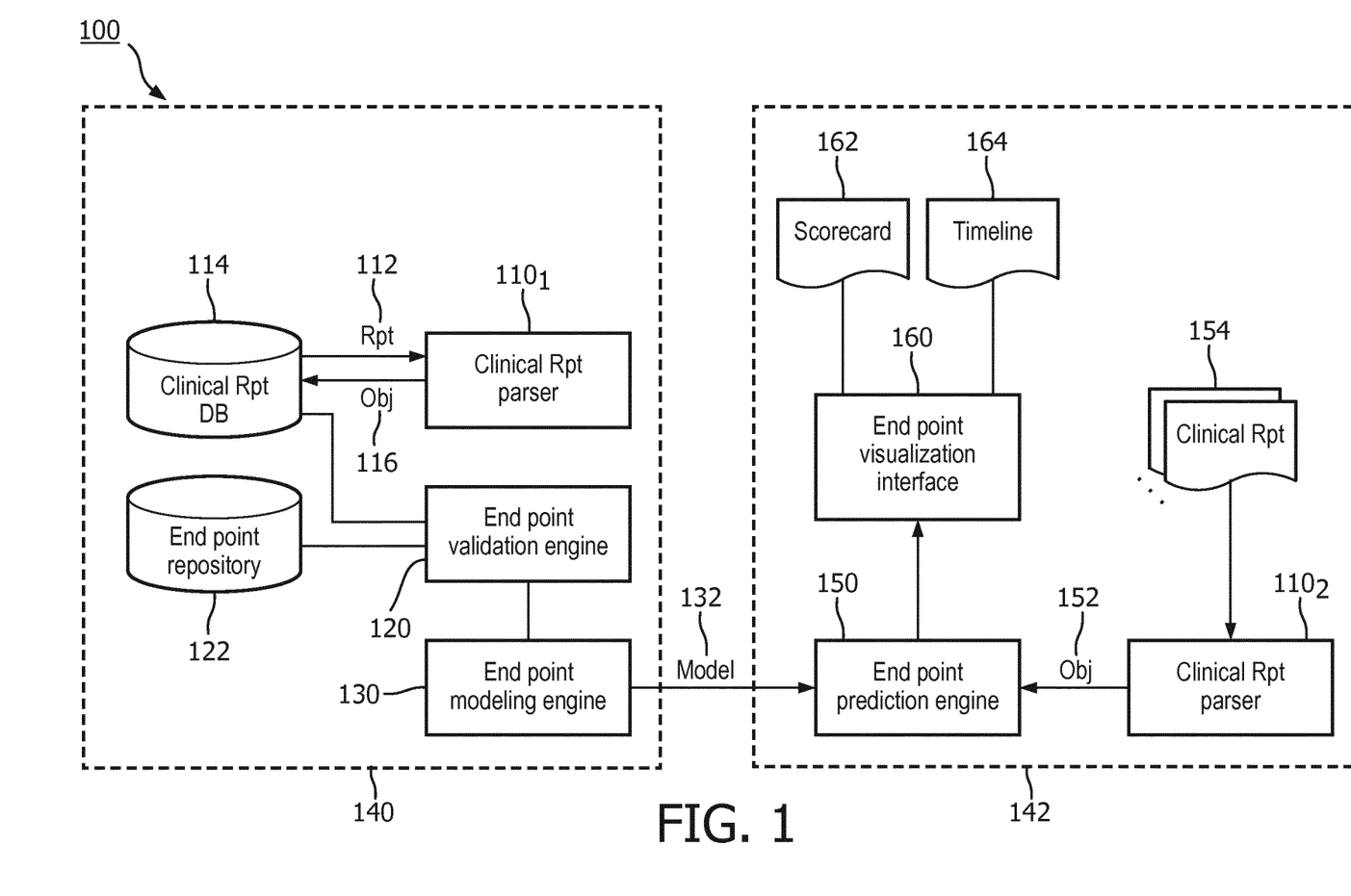
FIG. 1 schematically illustrates an embodiment of a system for summarizing clinical reports with end points.

With reference to FIG. 1, an embodiment of a system 100 for summarizing clinical reports with end points is schematically illustrated. A clinical endpoint is an external reference point that identifies a meaning or a main message of the summarized clinical reports, such as a diagnosis, a recommendation for a follow-up study, or a cost of a treatment. The clinical end point is a quantifiable parameter that can assume a finite number of discrete values. The clinical end point includes a predetermined time frame.

A clinical report parser 1101 receives clinical reports 112 from a clinical report database or repository 114, parses each clinical report 112, and generates a clinical report object 116 for each clinical report 112, such as in an EXtensible Markup Language (XML) or JavaScript Object Notation (JSON) format. The generated clinical report object 116 includes hierarchical ordering and identifying associated meta-data.

In one embodiment, the clinical report parser 1101 uses natural language processing (NLP) techniques to order the information in the clinical report object 116 and identify the associated meta-data. The NLP techniques can include detecting sentences, paragraphs and/or sections based on analysis of punctuation, new line or line returns, heading patterns, and combinations thereof. The NLP techniques can include detecting words, n-grams, phrases, and combinations thereof. The NLP techniques can include part-of-speech tagging, such as tagging a word or group of words as a noun, noun phrase, verb, predicate, and the like. For example, in the sentence "the mitral valve regurgitates", "mitral valve" is tagged as a noun phrase and "regurgitates" as a verb or a predicate. The NLP techniques can include concept extraction using an ontology, such as SNOMED, RadLex®, and the like. The hierarchical ordering organizes the information within the clinical report object 116, such that, e.g., sentences are grouped under paragraphs and sections, and words and phrases are grouped under sentences, etc. In some embodiments, the clinical report object 116 can include links to the clinical report 112, which map the detected section, paragraph, sentence, phrase, and/or word in the object to a corresponding spatial location in the report.

For example, in a diagnostic imaging study clinical report, a sentence "A lung nodule of six millimeters (6 mm) is present in the lower right lobe" is detected under a section heading of "Findings." The clinical report parser 1101 hierarchically orders the sentences and sections, and identifies under the "Findings" section heading the patient anatomy as "lung lower right lobe" in the meta-data of the clinical report object 116. The clinical report parser 110 further uses an ontology to extract the concept of the "nodule" with an ICD-10 diagnosis code, R91.1 tagged in the meta-data.

The clinical reports database 114 includes the clinical reports 112, such as radiology reports, pathology reports, surgical reports, oncology reports, and the like. In some embodiments, the clinical reports database 114 includes other patient related information, such as orders, billing records, prescriptions, electronic medical records, combinations and the like. The clinical reports 112 are time stamped with, for example, a date on which the report was produced, a date of the examination, and/or the like. The clinical reports database 114 can be indexed by patient identifier, time stamp, or combinations thereof. In some embodiments, e.g., the illustrated embodiment, the clinical reports database 114 includes the clinical report objects 116.

An end point validation engine 120 identifies validated clinical reports 112 to the clinical reports database 114 after validation of an end point for the clinical report 112. The end point validation engine 120 stores validated end points or representations thereof in an end point repository 122. For example, where a pathology clinical report confirms an oncological malignancy from a lung lesion biopsy for a patient, Bob Roberts—the end point validation engine 120 identifies the clinical reports 112 for Bob Roberts to the clinical report database 114. In some embodiments, the validation includes a review by a healthcare practitioner. In some embodiments, the validated end points are indexed in the repository 122 by patient, end point, or combinations thereof. In some embodiments, the end points and associated variables are stored in a relational table. The associated variables are data items, which are found to be predictive of the end point. For example, in an oncological malignancy diagnosis within a 30 day end point, associated variables include a history of smoking, and a plurality of lesions finding in a radiological report for a lung imaging study. In some embodiments, the associated variables include links to the hierarchically ordered information and/or meta-data in the clinical report objects 116.

In some embodiments, the end point is represented by information from which the end point can be derived. For example, in an end point of "a hospital cost of an episode of care greater than $10,000," individual costs are stored for the episode and a total cost is aggregated through a query of the individual costs. In some embodiments, the information representing an end point can be derived using NLP techniques. For example, for an end point of "oncological malignancy," radiology and pathology reports and/or objects can be processed using a combination of query and NLP techniques to obtain the end point and associate variables. In some embodiments, the end point validation engine 120 normalizes the end points. For example, for an oncological malignancy diagnosis within 30 days, end points can be normalized using an ontology and/or staging classification, such as ICD-10 diagnosis code, Breast Imaging, Reporting and Data System (BI-RADS) score, and the like. For end points of qualification for a screening program within 30 days, the end points can be normalized to particular screening programs or type of screening program, such as by sponsor.

The end point validation engine 120 uses rules to identify associated variables and/or relevant information items in corresponding clinical report objects 116 to validate end points. For example, an end point is an oncological malignancy diagnosed within 30 days. The clinical report object 116 is from a narrative radiology report. A rule identifies the end point of the radiology report as the end point of the closest pathology examination for the same patient anatomy following the radiology study that was conducted within one year. This rule means that if the closest pathology examination following the narrative radiology report within one year confirms the oncological malignancy, then one end point of the narrative radiology report is the oncological malignancy diagnosed within 30 days. In some instances, the rules act as a filtering mechanism to identify relevant report objects and discard irrelevant report objects. In some instances, the rules identify or associate end points for clinical report objects 116.

An end point modeling engine 130 models the validated end points in the end point repository 122 and the information from the relevant clinical report objects 116 using machine learning techniques to generate a machine learning model 132. For example, each phrase or n-gram from the relevant clinical report objects is presented in the form of a vector for the validated end point to the end point modeling engine 130. In some instances, this "convolutional" approach uses minimal "feature engineering" and layers of artificial neurons, each receiving input signals from a selection of proximal vector entries. Other suitable algorithms include deep learning, random forest, support vector machines, or logistic regression.

In some instances, the generated machine learning model 132 can distinguish based on associated variables, such as findings, statements, recommendations, or diagnosis between healthcare practitioners. For example, where training data includes an identity of a healthcare practitioner generating each clinical report 112, the model 132 can distinguish between same findings by different the healthcare practitioners. For example, the model can distinguish validated end points and in turn, identify different predictive scoring for oncological malignancy within 30 days according to clinical reports of different radiologists. In one example, the predictive end score for oncological malignancy within 30 days from summarized clinical reports created by radiologist 1 is 63% versus 75% and 98% for clinical reports created by radiologists 2 and 3, respectively, A higher predictive end score suggests better diagnostic skill.

The end point modeling engine 130 can operate in a periodic processing cycle 140 in which the training data from the end point repository 122 and the clinical report database 114 is updated or revised. For example, the end point modeling engine 130 can operate when the training data from the end point repository 122 and the clinical report database 114 changes more than a threshold percentage or the end point modeling engine 130 can operate on a weekly, monthly, quarterly, and/or annual cycle.

In an application cycle 142, such as real-time processing, an end point prediction engine 150 uses the generated machine learning model 132 to predict end points for clinical report objects 152 for a patient, which were not present in the training data. That is, the generated machine learning model 132 inputs new clinical report objects 152 and outputs predicted end points according to the phrases or n-grams in the new clinical report objects 152. The clinical report objects 152 are generated by a clinical report parser 1102 using newly received clinical report or reports 154. In some embodiments, the clinical report parser 1101 and the clinical report parser 1102 are the same parser, and in some embodiments they are different parsers. The end point prediction engine 150 summarizes the newly received clinical report 154 using a predicted end point(s). In some instances, the summarization is without restructuring of clinical reports and/or selective access to information items within a clinical report. In some embodiments, the end point prediction engine 150 processes all reports for a collection of patients in the application cycle 142. As described in greater detail below, the summary includes a scorecard 162 and/or a timeline 164, which are output via a display via an end point visualization interface 160.

In some instances, the scorecard 162 and/or timeline 164 summarizes a document, avoiding or minimizing overhead by report creators. For example, existing report generation including narrative documents can be utilized, rather than forcing a more structured approach. Furthermore, error margins are can be minimized by multi-value end points, prediction time frames and identification of text within each clinical report. The errors margins are reduced by using high confidence documents, such as pathology reports for validation. For example, in a predicted oncological malignancy diagnosed within 30 days, the underlying data or truth for the machine learning model are validated end points using pathology reports and clinical reports identified by rules associated the pathology reports, which minimize error margins. Additionally, the end point visualization interface 160 can directly identify, using links or text, narrative within the received clinical reports 154 that correspond to the result in the scorecard 162 and/or timeline 164. In some instances, the identified narrative can additionally provide a high confidence in the end point values when displayed for a healthcare practitioner.

Figure 2:
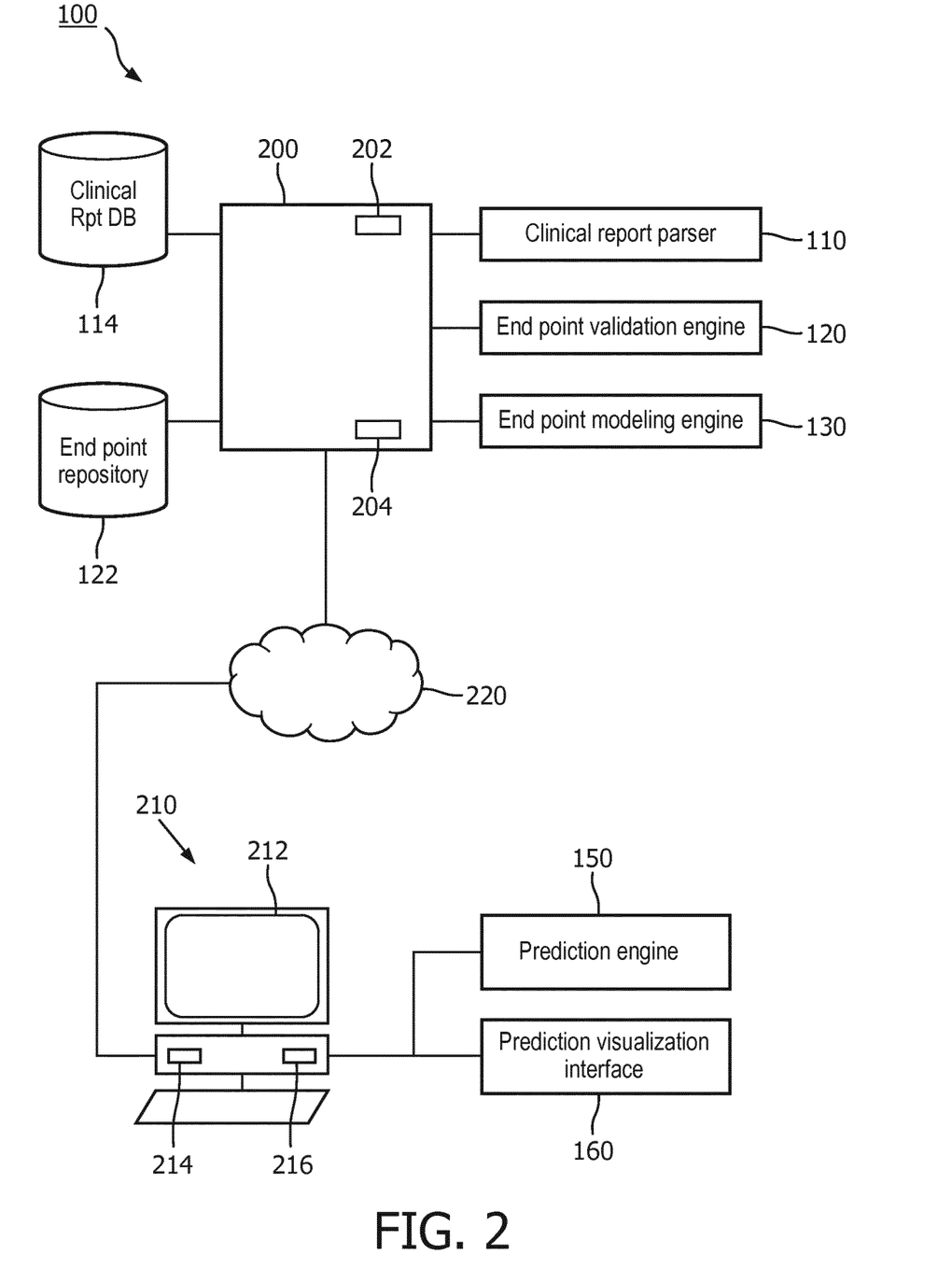
FIG. 2 schematically illustrates another embodiment of a system for summarizing clinical reports using end points.

With reference to FIG. 2, another embodiment of the system 100 for summarizing clinical reports using end points is schematically illustrated. The system 100 is configured in a client server arrangement with a server 200 and a computing device 210 communicatively connected over a network 220. In some embodiments, the system 100 is configured with a single computing device or multiple computing devices, such as combinations of servers and computer devices. The configuration can include the server 200 configured as a Hypertext Transfer Protocol Server (HTTP) or web server, and the client computer 210 configured with a web browser. The configuration can include the client computer 210 configured with "an app" and the server 200 configured to communicate with standard network protocol, such as IP protocols.

The clinical report parser 110, the end point validation engine 120, and the end point modeling engine 130 are illustrated as distributed parts of the server 200. The end point prediction engine 140 and the end point visualization interface 150 are illustrated as distributed parts of the computing device 210. In other embodiments, the distribution of the clinical report parser 110, the end point validation engine 120, the end point modeling engine 130, the end point prediction engine 140, and the end point visualization interface 150 between the server 200 and the computing device 210 varies. A varied distribution can include the engines 120, 130, 140, and the parser 110 being in one computing device. The varied distribution can include different combinations of the engines 120, 130, 140, and the parser 110 distributed between the server 200 and the computing device 210.

The network 220 can include wired and/or wireless communications, cellular and/or data communications, private and/or public networks, or combinations thereof.

The computer server 200 includes a processor 202 and a memory 204. The clinical report database 114 and the end point repository 122 are suitably embodied by a configured electronic storage medium, such as local disk, cloud storage, server storage, remote storage and the like, accessed by the configured computer processor 202. The configured electronic storage medium can include system file structures, relational and/or object oriented database system structures, and the like.

The computing device 210 includes a display device 212, a processor 214 and a memory 216. The computing device 210 can include a laptop, desktop, tablet, television (TV), smartphone, body worn device, and the like. The display device 212 is suitably embodied by a computer display, smartphone display, projector, body worn display, and the like.

The clinical report parser 110, the end point validation engine 120, the end point modeling engine 130, the end point prediction engine 140, and the end point visualization interface 150 are suitably embodied by the configured processors 202, 214, such as a digital processor, a microprocessor, an electronic processor, an optical processor, a multi-processor, a distribution of processors including peer-to-peer or cooperatively operating processors, client-server arrangement of processors, and the like, communicatively connected to the network 220 and configured to receive and convert the clinical reports 112, 154 to the clinical report objects 116, 152, validate, normalize and store end points, identify associated variables and/or relevant items in corresponding clinical report objects 116, 152, generate the machine learning model 132, predict end points, and visualize the predicted end points.

The configured processors 202, 214 execute at least one computer readable instruction stored in the computer readable storage medium 204, 216, such as an optical disk, a magnetic disk, semiconductor memory of a computing device with the configured processor, which excludes transitory medium and includes physical memory and/or other non-transitory medium to perform the disclosed techniques. The configured processor may also execute one or more computer readable instructions carried by a carrier wave, a signal or other transitory medium. The lines between components represented in the diagram represent communications paths.

In some embodiments, the clinical report parser 110, the end point validation engine 120, the end point modeling engine 130, the end point prediction engine 140, and the end point visualization interface 150 are suitably embodied as computer program products.

Figure 3:
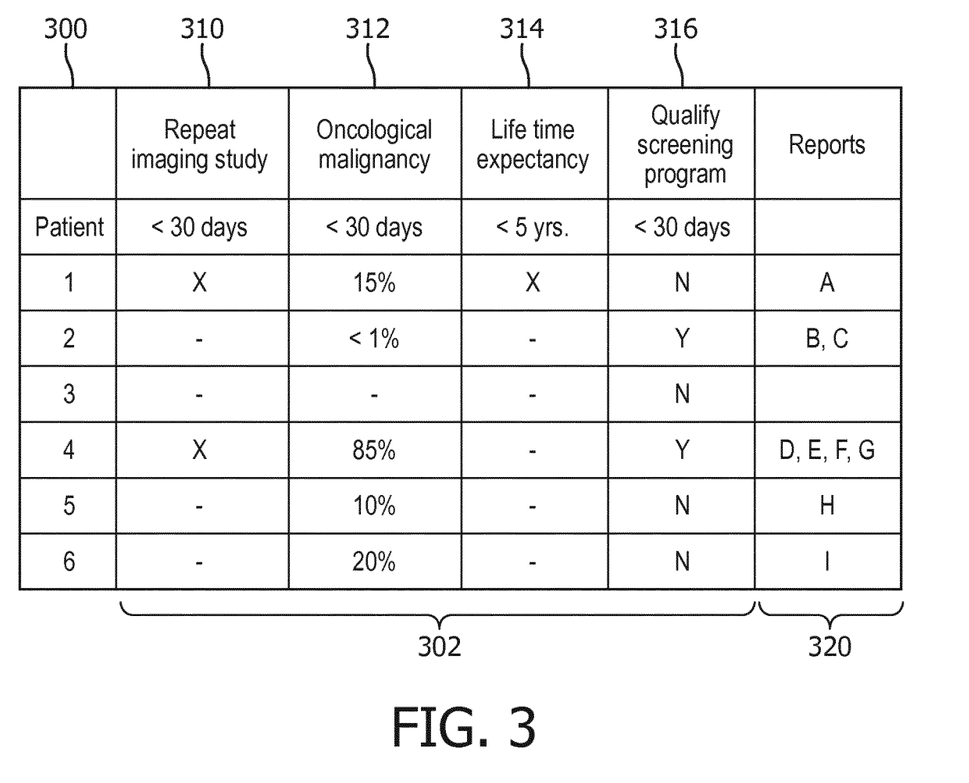
FIG. 3 illustrates an example of a displayed scorecard according to predicted end points.

With reference to FIG. 3, an example of a scorecard 300 is illustrated. The predicted end points 302 include a repeat imaging study to be performed within 30 days 310, an oncological malignancy diagnosed within 30 days 312, a life time expectancy within 5 years 314, and a qualification for a screening program within the next 30 days 316. Other examples of predicted end points 302 include an occurrence of a major cardiac event within 30 days, the hospital cost of an episode of care greater than $10,000 within one year, and a readmission within 30 days.

Each predicted end point 302 includes a quantitative binary or multi-value measure. The values in the scorecard 300 can be represented numerically, such as percentages or probabilities, or binary values, such as "Y" or "N", "X" or blank, and the like. The scorecard 300 can include a single end point, multiple end points for a patient, a single end point for multiple patients, or multiple end points for multiple patients as illustrated.

The scorecard 300 can include relevant clinical reports 320 determined relevant by the prediction engine 150. The relevant clinical reports 320 can include a subset of the newly received clinical reports 154. The relevant clinical reports 320 can be indicated with indicators that link to the spatial locations within the corresponding newly received clinical report 154. The links can be supplied via the clinical report object 152. In some embodiments, the portion of text, such as a phrase and/or sentence from the newly clinical report 154 can be supplied through the clinical report object 152.

In some embodiments, the scorecard 300 includes the predicted end points 302, each with a corresponding predetermined timeframe, and specific to a user profile. For example, a first end point of an oncological malignancy diagnosed within 30 days is included in a display of a first healthcare practitioner, such as a radiologist, and a second end point of a hospital readmission within 30 days is omitted. For a second healthcare practitioner, such as a hospital administrator planning bed allocations, the first end point is omitted and the second end point is included.

Figure 4:
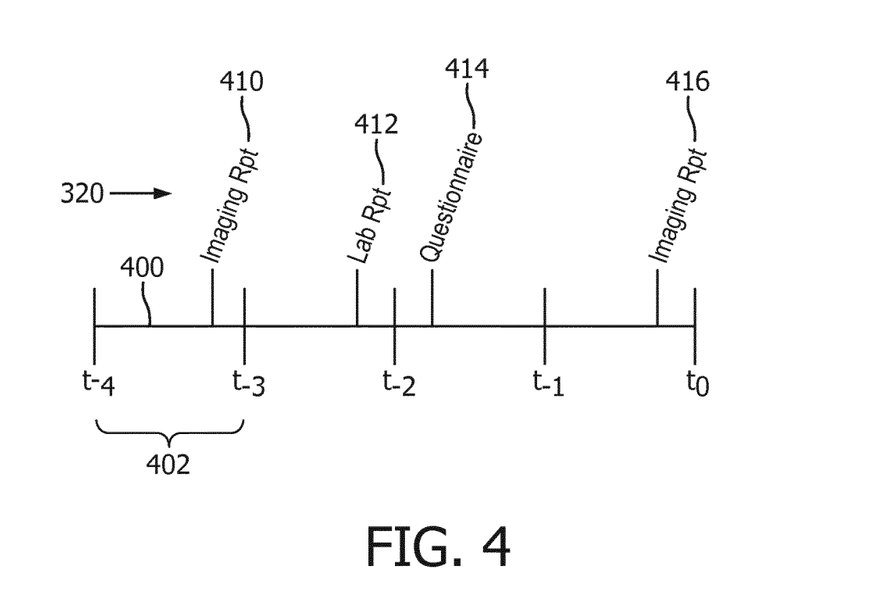
FIG. 4 illustrates an example of a displayed timeline of patient documents for a predicted end point.

With reference to FIG. 4, an example of a graphically displayed timeline 400 of patient clinical reports 154 for a predicted end point 302 is illustrated. In other embodiments, the displayed timeline 400 can be textually illustrated with a table of clinical reports 154 ordered chronologically.

The displayed timeline 400 includes time periods 402, such as days, weeks, months, or years and the like. The relevant clinical reports 320 are illustrated in relationship to the timeline, such as a point on the timeline or a line connected the individual relevant clinical report 320 to the timeline 400. For example, a first imaging study clinical report 410 is indicated between time indicators $t_4$ and $t_3$, a lab clinical report 412 is indicated between time indicators $t_3$ and $t_2$, a completed questionnaire clinical report 414 is indicated between time indicators $t_2$ and $t_1$, and a second imaging study clinical report 416 is indicated between time indicators $t_1$ and $t_0$. The time indicator $t_0$ can represent current time, or the time according to the end point 302. In some embodiments, the relevant clinical reports 320 can be indicated with icons. In some embodiments, the icons can indicate a value of the scorecard 300, such as with color, highlight, shape, symbols combinations and the like.

As with the relevant clinical reports 320 according to the scorecard 300, the relevant clinical reports 320 according to the timeline 400, such as the first imaging report 410, the lab report 412, the questionnaire 414, and the second imaging report 416 can include links, such as hyperlinks to the spatial locations or portions of text or information identified by the end point prediction engine 150.

Figure 5:
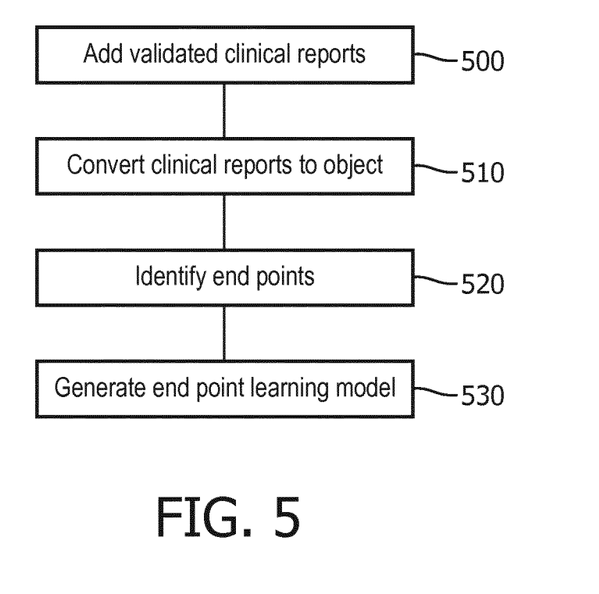
FIG. 5 flowcharts an embodiment of a method of generating a machine learning model for predicting end points.

With reference to FIG. 5, an embodiment of a method of generating a machine learning model 132 for predicting end points 302 is illustrated.

At 500, the clinical reports 112 of validated end points are identified to the clinical report database 114.

At 510, the clinical reports 112 are converted to clinical report objects 116, as described herein and/or otherwise.

At 520, the validated end points and associated variables are identified and added to the end point repository 114, as described herein and/or otherwise.

At 530, the end point learning model 132 is generated using machine learning techniques, as described herein and/or otherwise. The end point learning model 132 is structured to predict one or more end points 302, each within a predetermined time frame.

Figure 6:
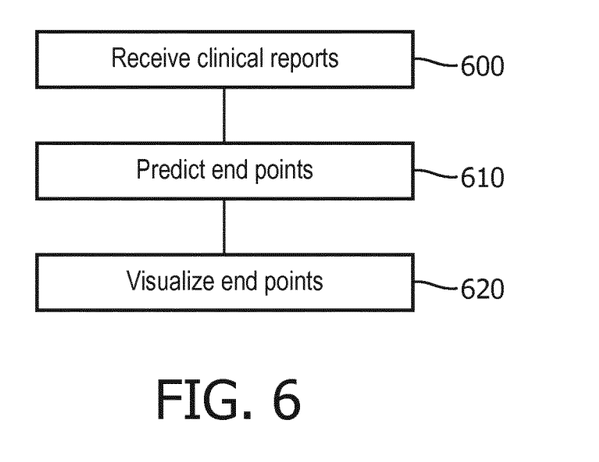
FIG. 6 flowcharts an embodiment of a method of summarizing clinical reports using end points.

With reference to FIG. 6, an embodiment of a method of summarizing clinical reports 154 using end points 302 is illustrated.

At 600, one or more clinical reports 154 are received for a patient and converted to the clinical report objects 152.

At 610, end points are predicted according to the clinical report objects 152 and the machine learning model 132, as described herein and/or otherwise.

At 620, the predicted end points 302 are visualized. The predicted end points 302 can be visualized using a scorecard and/or a timeline. The visualization can be specific to a healthcare practitioner profile.

The above may be implemented by way of computer readable instructions, encoded or embedded on a computer readable storage medium, which, when executed by a computer processor(s), cause the processor(s) to carry out the described acts. Additionally or alternatively, at least one of the computer readable instructions is carried by a signal, carrier wave or other transitory medium.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A system, comprising:
an end point validation engine comprising a first processor configured to determine relevant data and discard irrelevant data in one or more clinical report objects for a subject;
an end point prediction engine comprising a second processor configured to predict an end point using a machine learning model and the one or more clinical report objects for the subject, wherein the machine learning model inputs the one or more clinical report objects and outputs the predicted end point according to phrases or n-grams in the one or more clinical report objects,
wherein the machine learning model is based on a convolutional approach using minimal feature engineering, and
wherein the convolutional neural network applies at least one or more analytical techniques including deep learning, a random forest classifier, a support vector machine, and logistic regression; and
an end point visualization interface configured to visualize the predicted end point, wherein the predicted end point includes at least one of a repeated imaging study within a first predetermined time frame, an oncological malignancy diagnosed within a second predetermined time frame, a life time expectancy within a third predetermined time frame, a qualification for a screening program within a fourth predetermined time frame, an occurrence of a major cardiac event within a fifth predetermined time frame, a hospital cost of an episode of care greater than a predetermined amount within a sixth predetermined time frame, and a hospital readmission within a seventh predetermined time frame.

2. The system according to claim 1, further comprising:
a clinical report parser configured to receive clinical reports and generate the clinical report objects;
wherein the clinical reports comprise at least one selected from a group comprising of radiology reports, pathology reports, surgery reports, laboratory reports and progress reports.

3. The system according to claim 1, wherein the predicted clinical end points are visualized using a scorecard or a timeline.

4. The system according to claim 1, wherein the clinical report objects include n-grams representing phrases in the clinical reports.

5. The system according to claim 1, wherein the clinical report objects are formatted in extensible markup language (XML) or Javascript Object Notation (JSON).

6. The system according to claim 1, further comprising:
an end point modeling engine comprising a third processor configured to generate the machine learning model from training data that includes validated end points and clinical report objects.

7. A non-transitory computer-readable storage medium carrying instructions which controls one or more processors to:
determine relevant data and discard irrelevant data in one or more clinical report objects for a subject;
generate a machine learning model from training data that includes validated end points and clinical report objects, wherein the machine learning model is configured to:
predict an end point using the one or more clinical report objects for a subject, wherein the machine learning model inputs the one or more clinical report objects and outputs the predicted end point according to phrases or n-grams in the one or more clinical report objects,
wherein the machine learning model is based on a convolutional approach using minimal feature engineering, and
wherein the convolutional neural network applies at least one or more analytical techniques including deep learning, a random forest classifier, a support vector machine, and logistic regression; and
visualize the predicted end point, wherein the predicted end point includes at least one of a repeated imaging study within a first predetermined time frame, an oncological malignancy diagnosed within a second predetermined time frame, a life time expectancy within a third predetermined time frame, a qualification for a screening program within a fourth predetermined time frame, an occurrence of a major cardiac event within a fifth predetermined time frame, a hospital cost of an episode of care greater than a predetermined amount within a sixth predetermined time frame, and a hospital readmission within a seventh predetermined time frame.

8. The non-transitory computer-readable storage medium according to claim 7, wherein the one or more processors are further controlled to:
generate the clinical report objects from received clinical reports; and
wherein the clinical reports comprise at least one selected from a group comprising of radiology reports, pathology reports, surgery reports, laboratory reports and progress reports.

9. The non-transitory computer-readable storage medium according to claim 7, wherein the one or more processors are further controlled to:
validate the end points using a set of rules for each clinical report for a subject.

10. The non-transitory computer-readable storage medium according to claim 7, wherein the one or more processors are further controlled to:
predict an end point using the machine learning model for one or more clinical report objects for a subject.

11. The non-transitory computer-readable storage medium according to claim 10, wherein the one or more processors are further controlled to:

visualize the predicted end point for the subject using a scorecard or a timeline.

\* \* \* \* \*